(12) United States Patent
Trinh et al.

(10) Patent No.: US 7,243,509 B2
(45) Date of Patent: Jul. 17, 2007

(54) THERMAL THERAPEUTIC METHOD

(76) Inventors: David Lam Trinh, 8671 Creekwood La., Maineville, OH (US) 45039;
Dennis Sam Trinh, 8671 Creekwood La., Maineville, OH (US) 45039;
Albert Long Trinh, 8671 Creekwood La., Maineville, OH (US) 45039

( * ) Notice: Subject to any disclaimer, the term of this patent is extended or adjusted under 35 U.S.C. 154(b) by 149 days.

(21) Appl. No.: 11/229,942

(22) Filed: Sep. 19, 2005

(65) Prior Publication Data
US 2006/0010902 A1    Jan. 19, 2006

Related U.S. Application Data

(63) Continuation-in-part of application No. PCT/US2004/017792, filed on Jun. 4, 2004, and a continuation-in-part of application No. 10/455,885, filed on Jun. 6, 2003, now Pat. No. 7,096,687, and a continuation-in-part of application No. 10/455,886, filed on Jun. 6, 2003, now Pat. No. 7,065,983.

(51) Int. Cl.
F25D 3/08 (2006.01)
(52) U.S. Cl. .................................... 62/457.2
(58) Field of Classification Search .......... 62/457.2, 62/457.1, 457.4; 607/109, 111
See application file for complete search history.

(56) References Cited

U.S. PATENT DOCUMENTS

| | | | |
|---|---|---|---|
| 2,403,676 A | 7/1946 | Modlinski | |
| 2,882,692 A | 4/1959 | Robbins | |
| 2,898,744 A | 8/1959 | Robbins | |
| 2,925,719 A | 2/1960 | Robbins et al. | |
| 3,058,313 A | 10/1962 | Robbins | |
| 3,643,665 A | 2/1972 | Caillouette | |
| 3,780,537 A | 12/1973 | Spencer | |
| 3,885,403 A | 5/1975 | Spencer | |
| 3,889,684 A * | 6/1975 | Lebold | ............ 607/109 |
| 3,893,834 A | 7/1975 | Armstrong | |
| 3,900,035 A | 8/1975 | Welch et al. | |
| 3,950,789 A | 4/1976 | Konz et al. | |
| 3,980,070 A | 9/1976 | Krupa | |
| 4,033,354 A | 7/1977 | De Rosa | |
| 4,462,224 A | 7/1984 | Dunshee et al. | |
| 4,527,566 A | 7/1985 | Abare | |
| 4,676,247 A | 6/1987 | Van Cleve | |
| 4,856,651 A * | 8/1989 | Francis, Jr. | ............ 206/219 |
| 4,891,501 A | 1/1990 | Lipton | |
| 4,920,964 A | 5/1990 | Francis, Jr. | |
| 4,931,608 A | 6/1990 | Bills | |
| 4,986,076 A | 1/1991 | Kirk et al. | |
| 5,000,176 A | 3/1991 | Daniel | |
| 5,080,095 A | 1/1992 | Tungate | |
| 5,148,804 A | 9/1992 | Hill et al. | |
| 5,167,655 A | 12/1992 | McCoy | |

(Continued)

*Primary Examiner*—Melvin Jones

(57) ABSTRACT

This invention relates primarily to a therapeutic method comprising the use of a flexible outer cover that allows quick and easy alternating insertions of separate heat and cold packs, and is attached using an adhesive layer or safety pins to a garment at a location on the garment that is in close contact with an injured area of the body when the garment is worn, to provide alternating cold and hot or hot and cold therapeutic treatments and to a contrasting thermal device comprising a flexible outer cover for use in this method, and an article of manufacture comprising said flexible outer cover and other optional elements to form said contrasting thermal device.

23 Claims, 1 Drawing Sheet

U.S. PATENT DOCUMENTS

| | | |
|---|---|---|
| 5,215,080 A | 6/1993 | Thomas et al. |
| 5,274,865 A * | 1/1994 | Takehashi ........................ 5/644 |
| 5,366,492 A * | 11/1994 | Ueki ............................ 607/114 |
| 5,545,197 A | 8/1996 | Bowen |
| 5,605,144 A | 2/1997 | Simmons et al. |
| 5,697,962 A | 12/1997 | Brink et al. |
| 5,741,220 A | 4/1998 | Brink |
| 5,792,213 A | 8/1998 | Bowen |
| 5,843,145 A | 12/1998 | Brink |
| 5,887,437 A | 3/1999 | Maxim |
| 5,967,308 A | 10/1999 | Bowen |
| 5,984,951 A | 11/1999 | Weiss et al. |
| 6,036,004 A | 3/2000 | Bowen |
| 6,048,326 A | 4/2000 | Davis et al. |
| 6,083,254 A | 7/2000 | Evans |
| 6,361,553 B1 | 3/2002 | Bowen |
| 6,514,279 B1 | 2/2003 | Lavin, Jr. |
| 6,648,909 B2 | 11/2003 | Helming |

* cited by examiner

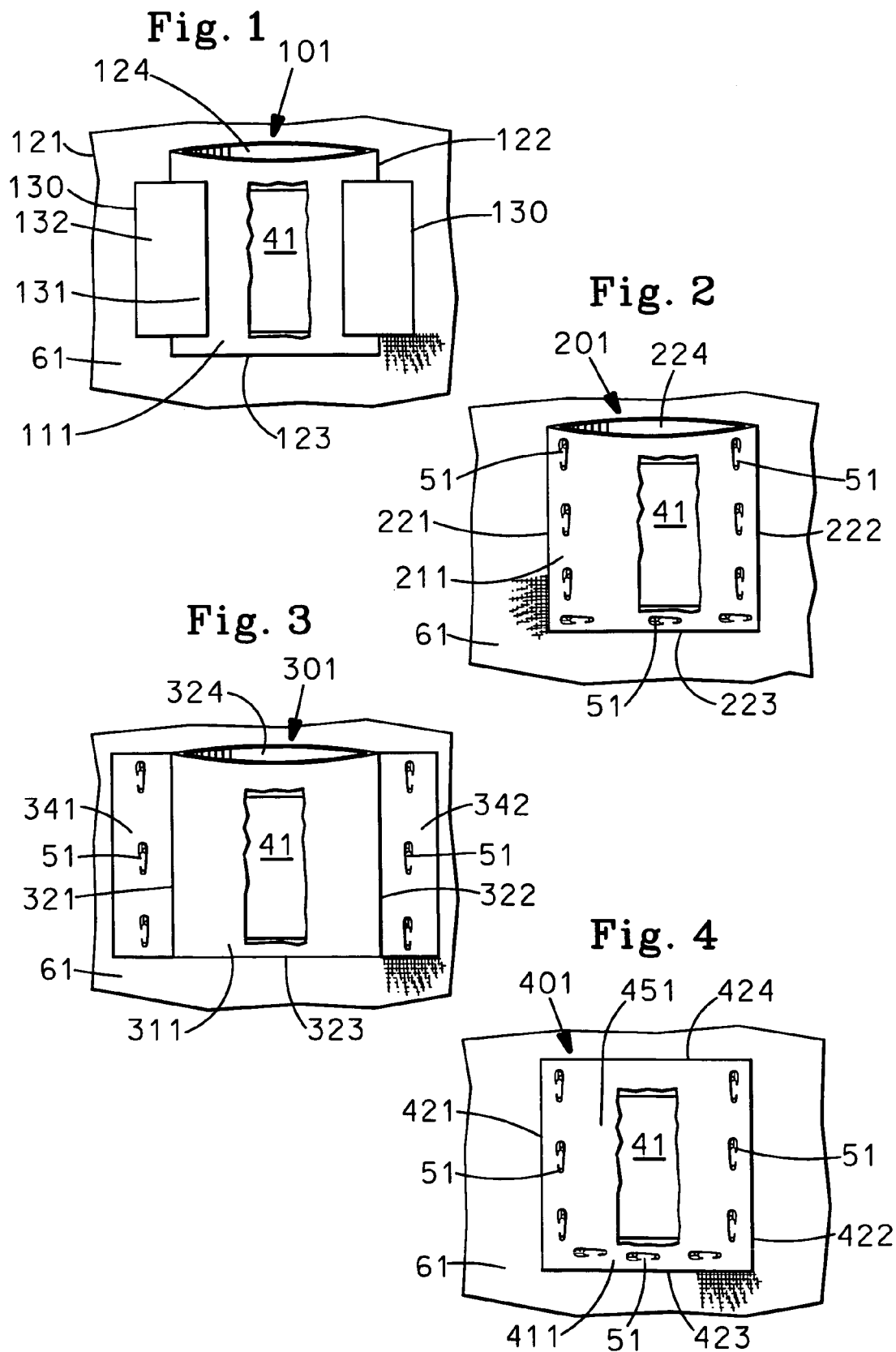

THERMAL THERAPEUTIC METHOD

This is a continuation-in-part of U.S. patent applications Ser. No. 10/455,885 now U.S. Pat. No. 7,096,687 and Ser. No. 10/455,886 now U.S. Pat. No. 7,065,983, Albert Long Trinh and David Lam Trinh, both filed Jun. 6, 2003 and claims priority from International Application No. PCT/US2004/017792, Albert Long Trinh and David Lam Trinh, filed Jun. 4, 2004.

BACKGROUND OF THE INVENTION

1. Field of the Invention

This invention relates to the general field of medical devices and methods for thermal treatment of, e.g., cooling and heating, injured body parts to, e.g., alleviate pain and inflammation. In particular, it relates to a novel method of using an improved cover for contrasting thermal treatments for therapeutic purposes, i.e., alternating cooling and heating applications, wherein the non-constrictive cover allows quick and easy alternating insertions of separate heating and cooling elements. It relates to a method of using thermal devices, e.g., a flexible cover optionally having an adhesive area or areas which can accept safety pins and which can be applied to an injured body part, either directly or indirectly by attachment to clothing, and a method of providing a thermal device comprising said cover that can be used to apply heat to an injured body part with improved comfort, convenience, and availability.

2. Description of the Related Art

The desirability of using ice bags and heating pads for thermal therapy is well accepted. It has long been an accepted medical practice to apply a cooling element to the surface of a body in the vicinity of an injury to, e.g., reduce swelling. Ice bags enable the user to apply cold to an injury such as a bruise or sprain without unacceptable mess. On the other hand, applying a heating element, such as a "heat pack", at the appropriate time can also improve the healing process.

A common ice bag that is commercially available is the reusable type comprising a water-impermeable, commonly a rubber-lined, flexible bag having a tubular rigid neck and a removable cap. To use, the bag is filled with ice cubes or ice chips and closed with the cap, then the bag is applied to the bruised area of the body and held it in place by hand. Another type of cold pack that is commercially available is a refrigeratable gel cold pack which comprises a refrigerant or coolant gel material contained in a plastic housing which can be either flexible or relatively inflexible. The gel packs are stored in a freezer for chilling or cooling and are then ready for use. Also commercially available is a chemical pack which comprises two or more pouches for separately storing chemical reactants which can be mixed to produce an endothermic cooling mixture. A common home-use ice bag can be made using a commercially available reclosable plastic sandwich or freezer bag with a zipper seal, such as a Ziploc™ plastic bag filled with ice (Ziploc is a registered trademark of Dow Chemical Company, Midland, Mich.). By "reclosable" it is meant that the bag can be open and closed numerous times.

Similarly, a common hot pack that is commercially available is a gel hot pack which comprises a gel material contained in a flexible plastic housing. The gel packs are heated, e.g., in a microwave oven to a desired temperature and are then ready for use. Also commercially available is a chemical hot pack which comprises two or more pouches for separately storing chemical reactants which can be mixed to produce an exothermic heating mixture. Other hot packs comprise an oxygen activated, heat generating chemical composition contained in a housing that allows air to permeate when heat is needed. A versatile thermal gel pack that is commercially available can serve both as a cooling bag and a heating bag when it is cooled in a household freezer and is heated in a microwave oven, respectively.

One of the disadvantages of many thermal bags is that they need to be inconveniently held by hand to maintain contact with the injured body part. To overcome this inconvenience, several types of thermal bag devices comprising a holder for these bags have been disclosed. Some ice bag devices can be strapped around a body part, with, e.g., loop and hook mating Velcro™-type fastening straps. A cold pack is disclosed having extended perimeter with adhesive means to attach said thermal pack to a skin surface. Yet other means to keep the ice bags in the proximity of the injured body part are also disclosed, such as a jacket with a plurality of attached pockets to hold the thermal packs. These and other ice bag devices are described in detailed in the BACKGROUND OF THE INVENTION section of U.S. patent application Ser. Nos. 10/455,885, 10/455,886, and 10/455,888, all filed Jun. 6, 2003. These ice bag devices are usually of complicated design, large and bulky in size and/or expensive to produce and/or difficult to be washed for reuse.

Thermal pack devices that support hot packs or both hot and cold packed are disclosed in U.S. Pat. No. 3,900,035 issued Aug. 19, 1976 to Welch et al.; U.S. Pat. No. 4,527,566 issued Jul. 9, 1985 to Abare; U.S. Pat. No. 4,676,247 issued Jun. 30, 1987 to Van Cleve; U.S. Pat. No. 5,000,176 issued Mar. 19, 1991 to Daniel; U.S. Pat. No. 5,605,144 issued Feb. 25, 1997 to Simmons et al.,; U.S. Pat. No. 5,741,220 issued Apr. 21, 1998 to Brink; and U.S. Pat. No. 6,514,279 B1 issued Feb. 4, 2003 to Lavin, Jr. These thermal pack devices are usually of complicated design, large and bulky in size and/or expensive to produce and/or difficult to be washed for reuse.

Recent medical practices call for alternating hot and cold therapy, in which alternating hot and cold packs are applied to the proximity of the injured area, to relieve many symptoms, such as arthritis, osteoarthritis, sciatica, chronic bacterial prostatitis, and back problems and injuries. This contrasting treatment calls for, e.g., a heat application for about 5 to about 20 minutes which is immediately followed by a cold application for about 5 to about 20 minutes, and the cycle is repeated several times daily. The thermal pack devices of the prior art do not provide a quick and easy change over from hot to cold and back to hot again. Furthermore, said devices are usually of complicated design, large and bulky in size and/or expensive to produce and/or difficult to be washed for reuse.

Thus, there is a need for a quick and facile method to provide the alternating hot and cold applications wherein the hot and cold packs can be interchanged rapidly and easily, especially without changing the position of the device, and the thermal pack device can be applied to the injured area without being held by hand. Preferably such thermal pack device is compact and not bulky, so that preferably it can fit in a first-aid box along with other first-aid items. Preferably such thermal pack device is easily manufactured and used.

SUMMARY OF THE INVENTION

This invention relates primarily to a method treating an injured area of the body, wherein said method comprises the use of a contrasting thermal device comprising a flexible outer cover that is suitable for use at both hot and cold temperatures and is either (A.) a sac structure with one open end having one face covered with a mounting adhesive layer that can be used to temporarily attach said outer cover to the inside or the outside of a garment, at a location on the garment that is in close contact with the injured area of the body, when the garment is worn, or (B.) a piece of flexible substrate or a sac structure with one or more open sides, optionally having one or more extended peripheries, said substrate or structure can be attached to the inside or the outside of a garment by the use of a plurality of safety pins, at a location on the garment that is in close contact with the injured area of the body, when the garment is worn, said structures being formed from material that is compatible with both cold packs and heat packs and being capable of holding at least one separate heat or cold pack, and wherein said method involves at least one step involving placing at least one cold pack or heat pack in the outer cover followed by removal of the said pack(s) and, optionally, replacing said first pack(s) by at least one heat or cold pack for treatment, the treatment comprising, e.g., cold being applied to the injured area for from about 3 minutes to about 1 hour, then replacing the cold pack with a heat pack in the outer cover to apply heat to the injured area for from about 3 minutes to about 1 hour, and optionally the cycle can be repeated several times with cold then hot treatments, and alternatively, the heat pack can be placed in the outer cover first to start with a hot treatment for from about 3 minutes to about 1 hour, then said heat pack is replaced by the cold pack in said outer cover to treat the injured area for from about 3 minutes to about 1 hour, and optionally followed with several cycles of hot and cold treatments.

The outer cover preferably has either a generally rectangular or square configuration when flattened. The outer cover can be made of material which is either woven, knitted, crocheted, non-woven fabric of natural and/or synthetic fibers, felt, velvet, flocked material, heat-bonded plastic fiber material, solvent-laid thermally bonded plastic fiber material, open-cell plastic foam, close-cell plastic foam, porous plastic film, nonporous plastic film, rubber, paper, and/or laminated materials, so long as the material is suitable for use at both hot and cold temperatures, that is the material retains acceptable properties when the temperature varies from, e.g., near the freezing point of water to about, e.g., from about 0° C. to about 80° C., or less, e.g., about 65° C. It is highly desirable that the material have good drape properties at low temperatures and good dimensional stability at elevated temperatures.

The outer cover with an adhesive layer A, has dimensions to form one or more compartments, preferably one compartment, that are suitable for containing one or more heat or cold packs, and wherein the adhesive layer can either cover one entire face of the outer cover or cover only part of that face or comprise one or more adhesive strips wherein said adhesive strips cover one or more edges of the outer cover and each adhesive strip has a width of at least about 1 cm, wherein the adhesive is suitable for use at both hot and cold temperatures, and wherein said adhesive layer and/or strips are optionally but preferably covered with a release layer. The outer cover optionally has from 1 to 4 extended peripheries from the edges of said outer cover, wherein each extended periphery is covered with an adhesive layer that can be used to temporarily attach said outer cover to a garment, in addition to or instead of the adhesive layer on the face of the outer cover; or has a periphery extended from the edge of the open end, wherein said periphery has an adhesive layer covering the reverse side of the periphery with respect to the mounting adhesive layer side, for use as a closing means to retain the hot and cold pack(s) in the outer cover; or wherein said adhesive layer is renewed after use by either using double-sided adhesive strips that are applied over the original adhesive layer or by removing the adhesive strips and replacing them with new strips.

The outer cover B, that uses safety pins to attach to the garment either has a generally tubular structure having two opposite open ends or a sac structure having three sealed sides and having the fourth side open, and wherein the cover has at least two extended peripheries extended from the two opposing sealed sides; or is a piece of substrate having extended peripheries on at least three sides.

The cold pack comprises a resealable or permanently sealed flexible plastic liquid impermeable container containing a cooling medium, wherein the cooling medium is ice; ice and water combination; water; refrigeratable cooling gel; or endothermic chemical cooling system. The heat pack comprises permanently sealed flexible plastic liquid impermeable or air permeable container containing a heating medium, wherein the heating medium is water; microwavable gel material; microwave-absorbing particulate matter; chemical reactants which can be mixed to produce an exothermic heating mixture; or oxygen activated, heat generating chemical composition.

In another aspect, the present invention relates to an article of manufacture for use in the thermal method of the present invention to provide contrasting thermal treatments, wherein the article comprises either one or more outer covers A.; or one or more outer covers B., and optionally a plurality of safety pins; and optionally one or more cold packs and optionally one or more heat packs; and optionally packaged in association with a set of instructions that tells a user how to use the cover to assemble a contrasting thermal device, and/or how to use the product properly, and/or to ensure that the user knows what benefits can be achieved, and/or how best to obtain these benefits, wherein the instructions are in one or more languages, and wherein the instructions are in words or words in combination with illustrative images and/or icons; preferably, said article comprises either one or more outer covers A.; or one or more outer covers B., and optionally a plurality of safety pins; and at least one other element which is either (a) one or more cold packs, one or more heat packs, or (b) said set of instructions, said cover or covers, said cold packs and/or heat packs and/or said instructions are packaged together.

The cold pack is select from: an empty zipper bag container to be filled with ice chips or ice cubes in use; refrigeratable cooling gel bag; and/or water impermeable flexible bag containing an endothermic chemical cooling system; and the heat pack is select from: a microwavable gel bag; flexible bag containing microwave-absorbing particulate matter; water impermeable flexible bag containing chemical reactants which can be mixed to produce an exothermic heating mixture; and/or air permeable flexible bag containing an oxygen activated, heat generating chemical composition.

The article comprising the outer cover A, is optionally packaged in association with a set of instructions which optionally comprises one or more of the following instructions: (a) place the outer cover on a location either inside or outside of a garment such that said cover is in close contact with the injured area of the body when the garment is worn; (b) attach the outer cover to the garment using the mounting adhesive layer; (c) attach the outer cover to the inside of the garment if there is room inside the garment to fit the complete alternating thermal device and/or if the garment is composed of one or more thick layers of fabrics, or attach the outer cover to the outside of the garment if the garment is made of thin material that allows good transmission of cold and heat to the injured body part and/or if there is not enough room inside the garment; (d) fill one or more plastic zipper bags with ice for use as the inner cold packs; (e) pre-cool one or more gel packs for use as the inner cold packs; (f) activate one or more chemical cold pack for use as the inner cold packs; (g) place the filled inner cold pack(s) in the compartment(s) of the outer cover; (h) close the open end of the outer cover with the extended periphery covered with adhesive, when said extended periphery is available; (i) wear the garment to apply the attached alternating thermal device over the injured part; (j) apply the cold treatment to the injured area for an effective time that is specified for different conditions normally requiring treatment, e.g., from about 3 minutes to about 1 hour; (k) heat one or more gel bags or bags containing microwave-absorbing particulate matter in a microwave oven; (l) activate the exothermic chemical systems; (m) replace the cold packs by the heat packs; (n) apply the heat treatment to the injured area for an effective time that is specified for the different conditions normally requiring treatment, e.g., from about 3 minutes to about 1 hour; (o) optionally the cycle can be repeated several times with cold then hot treatments; (p) alternatively, the heat pack can be placed in the outer cover first to start with a hot treatment, then said heat pack is replaced by the cold pack, and optionally followed with several cycles of heat and cold treatments; and/or (q) the instruction disclosing the non-constrictive nature and/or benefit of the contrasting thermal treatment. It is extremely important that adequate instructions be provided for articles of manufacture that are to be used by ordinary consumers who do not possess extensive medical training to treat a variety of conditions. Application of the wrong thermal treatment at the wrong time can result in aggravating a condition.

The article comprising the outer cover B, is optionally packaged in association with a set of instructions which optionally comprises one or more of the following instructions: (a) place the outer cover on a location either inside or outside of a garment such that said cover is in close contact with the injured area of the body when the garment is worn; (b) attach the outer cover to the garment using the safety pins, leaving the top side of the outer cover open to insert one or more inner cold and heat packs; (c) attach the outer cover to the inside of the garment if there is room inside the garment to fit the complete ice bag device and/or if the garment is composed of a thick layer, or attach the outer cover to the outside of the garment if the garment is made of thin material that allows good transmission of cold to the injured body part and/or if there is not enough room inside the garment; (d) fill one or more plastic zipper bags with ice and seal said bags for use as the inner cooling packs; (e) pre-cool one or more gel packs for use as the inner cooling packs; (f) activate one or more chemical cool packs for use as the inner cooling pack; (g) place the filled inner cooling pack(s) in the compartment(s) of the outer cover; (h) wear the garment to apply the resulting attached alternating thermal device over the injured part, (i) apply the cold treatment to the injured area for from about 3 minutes to about 1 hour, (j) heat one or more gel bags or bags containing microwave-absorbing particulate matter in a microwave oven; (k) activate the exothermic chemical systems; (l) replace the cold packs by the heat packs; (m) apply the heat treatment to the injured area for from about 3 minutes to about 1 hour; (n) optionally the cycle can be repeated several times with cold then hot treatments; (o) alternatively, the heat pack can be placed in the outer cover first to start with a hot treatment, then said heat pack is replaced by the cold pack, and optionally followed with several cycles of heat and cold treatments; and/or (p) the instruction disclosing the non-constrictive nature and/or benefit of the contrasting thermal treatment.

In another aspect, the present invention relates to a therapeutic device for providing contrasting thermal treatments according to the thermal method of the present invention, wherein said device comprises: (a) a flexible outer cover; (b) at least one cold pack or materials for creating a cold pack selected from: resealable fluid impermeable plastic containers comprising an interlocking rib and groove sealing closure, optionally being a commercially available zipper bag, to contain ice or ice and water mixture; a refrigeratable cooling gel pack; or an endothermic chemical cold pack; and at least one heat pack or materials for creating a heat pack selected from: microwavable gel bag; flexible bag containing microwave-absorbing particulate matter, water impermeable flexible bag containing chemical reactants which can be mixed to produce an exothermic heating mixture; or air permeable flexible bag containing an oxygen activated, heat generating chemical composition; and (c) optionally, for outer cover B., either from about 1 to about 20 safety pins or from about 4 to about 12 safety pins.

The present invention also relates to a heat treatment method and an article of manufacture comprising the thermal therapeutic device of the present invention comprising an outer cover which is suitable for containing one or more heat packs and at least one heat pack which is placed in said outer cover to provide a heat treatment.

BRIEF DESCRIPTION OF THE DRAWINGS

FIG. 1 is a perspective view of a contrasting thermal device of the present invention, in an open configuration, comprising a flexible outer cover with a pouch structure having one open (top) end, and containing an inner thermal pack, showing the thermal device being secured to the garment with separate adhesive tapes, said outer cover being partly cut away to show said thermal pack;

FIG. 2 is a perspective view of an alternative embodiment of the contrasting thermal device of the present invention, in an open configuration, comprising a flexible outer cover with a tubular structure having two open ends, holding an inner thermal pack, showing the thermal device being attached to the garment with a plurality of safety pins, with the pins securing the two opposing closed sides and the bottom open side, and leaving the top side open for alternatingly replacing the thermal packs, said outer cover being partly cut away to show said thermal pack;

FIG. 3 is a perspective view of an alternative embodiment of the contrasting thermal device of the present invention, in an open configuration, comprising a flexible outer cover with a pouch structure having one open (top) end and two extended peripheries from the two opposing close sides, holding an inner thermal pack, showing the thermal device being attached to the garment with a plurality of safety pins, with the pins securing the two extended peripheries, said outer cover being partly cut away to show said thermal pack; and FIG. 4 is a plan view of an alternative embodiment of the contrasting thermal device of the present invention comprising a flexible outer cover comprising a rectangular piece of flexible substrate, holding an inner thermal pack, with a plurality of safety pins securing said outer cover to a garment on three sides, and leaving the top side open for alternating the hot and cold thermal packs by replacing one thermal pack with another thermal pack that is the same or different, said outer cover being partly cut away to show said thermal pack.

Other non-limiting alternative embodiments of the contrasting thermal device of the present invention are illustrated in FIG. 1 and FIG. 3 of U.S. patent application Ser. Nos. 10/455,885, which are shown with brief descriptions as paragraphs [0013] and [0015] on page 2 of U.S. Pat. Appl. Pub. No. U.S. 2004/0244412 A1 Dec. 9, 2004, and in FIG. 1 to FIG. 22 of U.S. patent application Ser. Nos. 10/455,886, which are shown with brief descriptions as paragraphs 100171 to [0038] on pages 2 and 3 of U.S. Pat. Appl. Pub. No. U.S. 2004/0244413 A1 Dec. 9, 2004, with the understanding that where a cold pack is shown, it can be replaced with a heat pack to alternate treatments, and all said patent applications and Patent Application Publications are incorporated herein by reference.

DETAILED DESCRIPTION OF THE INVENTION

This invention relates to a method to provide contrasting thermal treatments for therapeutic purposes, i.e., alternating hot and cold applications to an injured area of the body in a way that is fast and convenient, using a hot and cold contrasting thermal device, hereafter "thermal device", comprising a flexible outer cover and separate inner hot and/or cold packs, hereafter "thermal packs".

The outer covers for the hot and cold contrasting thermal devices that are useful in the present invention are described in details, including their drawings in U.S. patent application Ser. No. 10/455,885 filed Jun. 6, 2003 (FIG. 1 and FIG. 3), and Ser. No. 10/455,885 filed Jun. 6, 2003 (FIG. 1 to FIG. 22), incorporated herein by reference, with the understanding that where a cold pack is shown, it can be replaced with a heat pack or alternating heat and/or cold packs. As disclosed in paragraph [0208] of the PCT Publication WO 2005/000185 A2 which is published on 6 Jan. 2005 of our International Application No. PCT/US2004/017792 filed 4 Jun. 2004, the ice bag devices disclosed therein can be used with heat sources: "It is a special advantage of the ice bag devices herein, that the cover can be made heat resistant and then used for subsequent follow up treatment of injuries with heat by simply removing the cooling pack and inserting therefore one, or more heat sources. The change can be made without removing the cover in many instances. One readily available heat source for use in the present invention is an inner bag comprising one or more reclosable plastic bag with zipper seal containing hot water. A preferred heat source is gel packs that can be heated, e.g., in a household or hotel microwave oven. Many such gel packs are available commercially, and can be used as a heat source by heating up in a microwave oven and as a cooling source by being stored in, e.g., a conventional household freezer. Another preferred heat source is chemical packs that contain an exothermic chemical system that can generate heat, e.g., by mixing different ingredients together, or by being exposed to ambient air, to undergo an exothermic reaction. Alternatively, the present invention also relates to a thermal therapeutic device comprising a flexible outer cover of the present invention, preferably a non-constrictive outer cover, and a separate heat source comprising an inner container containing a heating medium to treat injuries and/or pain with heat only, without first going through a cold treatment. The present invention also relates to a heat treatment method and an article of manufacture comprising the thermal therapeutic device comprising a heat source of the present invention."

"Alternating cold and hot applications" and "alternatingly", as used herein, means that the injured body part is placed in contact with either (a) one or more cold packs either together or sequentially for a certain duration, typically from about 3 minutes to about 60 minutes, preferably from about 5 minutes to about 40 minutes, more preferably from about 10 minutes to about 30 minutes to provide a cold treatment, then said cold packs are replaced by one or more hot packs either together or sequentially, which are placed in contact with the injured body part for a certain duration, typically from about 3 minutes to about 60 minutes, preferably from about 5 minutes to about 40 minutes, more preferably from about 10 minutes to about 30 minutes, to provide a hot treatment, and optionally the cold and/or hot treatments are repeated for several cycles, with or without some intervals of no treatment in between, or (b) one or more hot packs for a certain duration, typically from about 3 minutes to about 60 minutes, preferably from about 5 minutes to about 40 minutes, more preferably from about 10 minutes to about 30 minutes, then said hot packs are replaced by one or more cold packs which are placed in contact with the injured body part for a certain duration, typically from about 3 minutes to about 60 minutes, preferably from about 5 minutes to about 40 minutes, more preferably from about 10 minutes to about 30 minutes, and optionally the hot and cold treatments are repeated for several cycles, with or without some intervals of no treatment in between. This general method of alternating heat and cold applications is also called "contrasting thermal treatments."

The present invention relates to a method to provide alternating cold and hot applications to an injured body part using a flexible outer cover that is temporarily attached to the inside or the outside of a garment, at a location on the garment that is in close contact with the injured area of the body, when the garment is worn, without the need for a strapping and/or wrapping means, said cover being attached to the garment by an adhesive or safety pins, or optionally for the adhesive, to the body, to provide alternating cold and hot treatments to the injured area, and wherein said cover has a sac structure (or pouch structure) having appropriate dimensions to form one or more compartments suitable for inserting and containing one or more inner hot or cold packs containing a heating and cooling media, wherein the hot and cold packs can be easily and quickly inserted into the outer cover and interchanged from hot pack to cold pack, and vice versa, and wherein the flexible outer cover is suitable for use at both hot and cold temperatures.

"Garment", as used herein, means any piece of clothing that is worn to cover a part of the body, such as shirt, jacket, coat, pants, trousers, shorts, underwear, hat, headband, sock, scarf, glove, and the like. The method of the present invention does not require any specially designed garment that is created for special use, e.g., with immovable pockets, with the sole purpose to hold the thermal packs. The method of the present invention is versatile and convenient, in that any garment can be used, as long as said garment covers the injured area of the body.

A special advantage of the method of the present invention is the ability to exchange one thermal pack for another thermal pack without changing the placement of the cover. This allows one to continue one thermal (e.g., cold) treatment for the appropriate period of time and an alternating thermal (e.g., heat) treatment in a simple, convenient, and efficient process that minimizes problems and potential errors.

I. Non-Constrictive Adhesive Attachment System

This invention, in this aspect, relates to a method to provide alternating hot and cold applications to an injured body part that is fast and convenient, using a flexible outer cover having a layer of mounting adhesive for use to temporarily attach said outer cover to the inside or the outside of a garment, at a location on the garment that is in close contact with the injured area of the body, when the garment is worn, without the need for a strapping and/or wrapping means, and wherein said cover has a sac structure (or pouch structure) having appropriate dimensions to form one or more compartments suitable for inserting and containing one or more inner heat or cold packs containing a heating and cooling media, wherein the heat and cold packs can be easily and quickly inserted via an open end into the outer cover and interchanged from hot pack to cold pack, and vice versa.

The flexible outer cover is preferably a unitary structure, typically either a sac structure (or pouch structure) with one open end to receive one or more thermal packs which comprise cooling packs and heating packs. The outer cover has a top open end (or optionally an open side) for permitting the inner cold and heat packs to be interchangeably inserted therewithin. The inner thermal pack is a separate structure that is not permanently attached to the outer cover. The outer cover can have any suitable shape such as rectangular, square, round, oval, and the like. Preferably the flexible outer cover has a generally rectangular or square configuration when flattened to facilitate storage and to more efficiently contain typical inner cooling and heating packs.

In a preferred embodiment, the outer cover is provided with an adhesive layer which is an integral part of the outer cover and entirely or partially covers one side of the outer cover to form a self-adhering outer cover. The construction of the outer cover and the locations of the mounting adhesive layer are described in details in U.S. patent application Ser. No. 10/455,886 filed Jun. 6, 2003, which is incorporated in its entirety herein by reference.

In another preferred embodiment, the outer cover is not self-adhering, with the adhesive layer being separated from the outer cover and being in the form of one or more adhesive strips that are used to attach the outer cover to the garment. Non-limiting examples of adhesive strips that are useful in the contrasting hot and cold thermal device of the present invention include sport tapes and bandage adhesive tapes that are commonly provided in roll form, adhesive bandage strips such as Band-Aid™ strips, adhesive tape such as Scotch™ tape, mailing tape, packaging adhesive tape, duct tape, masking tape, or the like, preferably bandage adhesive tape and/or sport tape.

When the mounting adhesive layer is an integral part of the outer cover, it is preferably covered with a peel-away release layer to protect it from prematurely sticking to a surface other than the intended user's garment. The release layer is preferably made of plastic film or other materials such as paper that can be coated with wax or other compositions for improved release. The release layer can extend beyond the outer edge of the adhesive layer to facilitate the removal of the release layer from the adhesive. The adhesive that is useful in the present invention needs to be suitable for use at both hot and cold temperatures, that is, it needs to retain acceptable adhesive properties when the temperature varies from, e.g., near the freezing point of water to about 80 degrees centigrade, e.g., from about 0 degree centigrade to about 80 degrees centigrade, or less, e.g., about 60 degrees centigrade. The adhesive that is useful in the present invention is typically an adhesive used in adhesive tapes, such as bandage adhesive tapes, sport tapes, Scotch™ tapes, mailing tapes, packaging adhesive tapes, duct tapes, masking tapes, or the like, preferably bandage adhesive tapes and sport tapes. The adhesive is preferably hypoallergenic. Preferably the mounting adhesive has a stronger bond to the outer cover surface than the release layer and the garment surface so that after use, when the thermal device is removed from the garment, the adhesive layer stays with the cover, and is not transferred to the garment. However, the bond with the garment surface should be strong enough to attach the thermal device well to the garment surface.

The outer cover is made at least partly of a relatively flexible substrate. The substrate is typically a fabric, normally woven and/or non-woven and/or knitted, but can also be a resilient foam sheet The outer cover can be made of material such as, but not limited to, woven, knitted, crocheted, or non-woven fabric of natural and/or synthetic fibers such as cotton, polyester, nylon, acrylic, rayon, and the like, felt, velvet, flocked material, heat-bonded plastic fiber material, such as, melt-blown, spun-bonded polyethylene or polypropylene, carded thermo-bonded polypropylene and rayon blend, solvent-laid thermally bonded polypropylene (e.g., Tyvek™ by Dupont), resilient open-cell or close-cell plastic foam sheet, porous and nonporous plastic film and/or rubber, paper, laminated materials such as laminate of rubber and non-woven layers, and the like, so long as the material is suitable for use at both hot and cold temperatures, that is, the material retains acceptable properties when the temperature varies from, e.g., near the freezing point of water to about 80 degrees centigrade, e.g., from about 0 degree centigrade to about 80 degrees centigrade, or less, e.g., about 60 degrees centigrade. It is highly desirable that the material have good drape properties at low temperatures and good dimensional stability at elevated temperatures. The preferred material makes the outer cover of the ice bag device flexible, conformable, and optionally stretchable, at least on the side that is in contact with the body. The material that contacts the body also preferably slows the cooling and/or the heating of the body part to avoid damage by overcooling, e.g., frostbite and/or burn. However, the material should allow heat to flow from and to the injured body part. Preferably, the material does not allow heat to flow through it at a rate that will result in frostbite and/or burn. The desired effect is cooling without freezing and heating without burning, and the cooling and heating are preferably at a rate that creates no more pain than can be withstood by the user and which does not cause damage to the treated area.

The mounting adhesive layer can either cover one entire face of the outer cover as is depicted in FIG. 1 of U.S. patent application Ser. No. 10/455,886, or cover only part of that face, preferably as adhesive strips that cover one or more edges of the outer cover, more preferably two adhesive strips that cover two opposite edges, as are depicted in FIG. 6 and FIG. 7, or one or more adhesive strips that cover all four edges of the outer cover, as are depicted in FIG. 8, all of U.S. patent application Ser. No. 10/455,886. The adhesive strips preferably have a suitable width to keep the ice bag device securely attached to the garment. Typically the adhesive strips have a width of at least about 0.5 cm, preferably at least about 1 cm, and more preferably at least about 1.5 cm. In a preferred embodiment, the outer cover has from 1 to 4 extended peripheries (or extended edges) that are extensions from the edges of the outer cover, and are covered with an adhesive layer for use to attach the outer cover to the garment, in addition to or instead of the adhesive layer on the body of the outer cover, as are depicted in FIG. 9, FIG. 12, and FIG. 14 of U.S. patent application Ser. No. 10/455,886. Each extended periphery along each edge can have a length that is shorter, but more preferably equal or longer than the corresponding edge. The periphery extension typically has a width of at least about 1 cm, preferably at least about 1.5 cm, more preferably at least about 2 cm, and less than about 20 cm, preferably less than about 8 cm, and more preferably less than about 6 cm. Optionally, the outer cover can have a periphery extended from the edge of the open end, with this periphery having an adhesive strip covered the reverse side of the periphery, with respect to the mounting adhesive layer side, for use as a closure means to tightly contain the inner thermal pack in the compartment of the outer cover, as is depicted in FIG. 20 of U.S. patent application Ser. No. 10/455,886. This adhesive closure means can optionally be replaced by loop and hook mating Velcro-type fastener strips.

In an alternative embodiment, the outer cover can be reused by renewing the original adhesive layer after use. This can be achieved by using double-sided adhesive strips that are applied over the original adhesive layers or where the original adhesive layers were placed after they are removed. It is preferred that the adhesive of the double-sided adhesive strips adhere more strongly to the outer cover than to garments or skin to facilitate removal. Replacing the tape can improve adherence to the cover when some of the adhesive remains on the cover after the double-sided tape is removed from the cover after use.

When the adhesive layer is a separate element from the outer cover, it can be provided by, e.g., a sport tape, or a bandage adhesive tape used for making bandages, by attaching part (a segment) of one or more strips of tape to the outer cover and another part to the clothing. Such sport tape and bandage adhesive tape is available typically in the form of a roll. Other types of adhesive tape, such as Scotch™ tape, mailing tape, packaging adhesive tape, duct tape, masking tape, or the like, can also be used if they are available.

Shown in FIG. 1 of the current invention is a view of an embodiment of the contrasting thermal device of the present invention, designated as 101, comprising a flexible outer cover 111 with a pouch structure in an open configuration having one open (top) end 124, three closed sides 121, 122, and 123, and two separate adhesive strips 130. A part (or a segment) 131 of the adhesive tape is attached to the outer cover 111 of the thermal device 101, and another part 132 is attached to garment 61. The top open end 124, which can optionally be oriented side way, is used for inserting and alternatingly replacing the thermal packs 41.

In another embodiment, the present invention relates to the option of using double-sided adhesive tape to attach an ice bag device to the garment by attaching one side of the double-sided adhesive tape strips to the outer cover at positions on the cover similar to the adhesive strips depicted in FIGS. 6-8 in U.S. patent application Ser. No. 10/455,886, and using the other side of the double-sided adhesive tape to attach the ice bag device to a garment.

Specific embodiments of the contrasting thermal device of the present invention given hereinabove are illustrated in FIG. 1 to FIG. 22 of U.S. patent application Ser. Nos. 10/455,886, which are shown with descriptions as paragraphs 100911 to 101031 in pages 9 to 11 of U.S. Pat Appl. Pub. No. U.S. 2004/0244413 A1 published Dec. 9, 2004, with the understanding that where a cold pack is shown, it can be alternated with, or replaced by, a heat pack, and said patent application and patent application Publication are incorporated herein by reference.

The outer cover can most conveniently have one compartment designed to have dimensions suitable to alternatively hold one inner cooling pack comprising an at least relatively liquid impermeable inner container containing a cooling medium and one inner heating pack containing a heating medium. The inner cooling pack and the inner heating pack can be inserted into the compartment through the open end of the outer cover. The outer cover can also be divided into two or more compartments to hold two or more inner cooling packs as described in U.S. patent application Ser. No. 10/455,886.

Each cooling pack comprises either a resealable or a sealed fluid impermeable, preferably plastic, container containing a cooling medium, such as a cooling gel, or an endothermic chemical system. Each heating pack comprises, e.g., either a sealed fluid impermeable, preferably plastic, container containing a heating medium, such as a microwavable heating gel, or a container containing an exothermic chemical heating mixture.

The inner cooling pack is preferably composed of a resealable or permanently sealed plastic liquid impermeable container containing a cooling medium, as described in U.S. patent application Ser. No. 10/455,886, wherein said cooling medium is preferably either ice, ice and water combination, water, refrigeratable cooling gel, or endothermic chemical cooling system. Ice, and ice and water mixture are preferably contained in a resealable or reclosable plastic container, such as a reclosable zipper bag, which is conveniently either a commercially available reclosable zipper bag such as a sandwich or freezer zipper bag, or a specially made zipper bag of any suitable size and thickness. The use of a reclosable bag allows one to replace the cooling medium when it is no longer cool. A refrigeratable cooling gel and/or an endothermic chemical cooling system are preferably contained in permanently sealed plastic containers. The permanently sealed plastic container can also contain liquid water to be placed in, e.g., a conventional freezer to form ice for use in the method and/or article of the present invention. In this embodiment, provision should be made for the expansion of the water when it freezes, either by having sufficient void space or by making the container expansible. Nonlimiting examples of reclosable zipper bag, refrigeratable cooling gel pack, and endothermic chemical cooling pack are described in details in U.S. patent application Ser. No. 10/455,886.

The inner heat pack is preferably comprised of a gel hot pack which comprises either (a) water or preferably a gel material contained in a flexible and liquid impermeable plastic housing and is heated, e.g., in a microwave oven to a desired temperature, typically hot to the touch, between from about 40° C. to about 80° C., preferably from about 45° C. to about 70° C., and more preferably from about 50° C. to about 65° C., and is then ready for use, (b) a flexible container containing a microwave-absorbing particulate matter, (c) a chemical heat pack which comprises either two or more pouches for separately storing chemical reactants which can be mixed to produce an exothermic heating mixture, or (d) an oxygen activated, heat generating chemical composition contained in a housing that allows air to permeate when heat is needed. A versatile thermal gel pack that is commercially available can serve both as a cold pack and a heat pack when it is cooled in a household freezer and is heated in a microwave oven, respectively.

A non-limiting example of a suitable microwavable heat pack is disclosed in U.S. Pat. No. 4,920,964 issued May 1, 1990 to Francis, Jr; this heat pack contains a gel with a composition of about 0.7% Carbopol™, about 27% propylene glycol, about 0.09% color dye, about 0.2% formaldehyde, about 1.0% sodium hydroxide, and the balance is water. Non-limiting examples of a gel pack that is suitable for both cooling and heating include a pack containing an aqueous gel comprising from about 20% to about 30% 1,3-propylene glycol and about 22% of a cellulose-based colloidal dispersion media, such as hydroxypropyl methylcellulose, as is described in U.S. Pat. No. 6,083,254 issued Jul. 4, 2000 to Evans, and an aqueous gel comprising about 36 parts of propylene glycol and 1 part of a superabsorbant polymer in about 156 parts of water, as is described in U.S. Pat. No. 5,843,145 issued Dec. 1, 1998 to Brink. A non-limiting example of a suitable heat pack that contains a microwave energy-absorbing particulate matter is disclosed in U.S. Pat. No. 4,931,608 issued Jun. 5, 1990, wherein the microwave absorbing particulate matter is selected from the group consisting of aluminum oxide, ferrites and garnets. A non-limiting example of an exothermic chemical system heat pack include a hot pack comprising a first chemical such as sodium acetate or sodium thiosulfate and a second chemical such as borax or aluminum oxide, as is described in U.S. Pat. No. 6,648,909 B2 issued Nov. 18, 2003 to Helming. Other suitable systems that include a solute and a solvent that produce heat when they are mixed together, such as calcium chloride and water, are given in U.S. Pat. No. 4,462,224 issued Jul. 31, 1984 to Dunshee et al. Non-limiting examples of air-activated exothermic chemical system include a flexible packet that contains a mixture of iron powder, activated charcoal, salt, water and wood fibers, as is described in U.S. Pat. No. 5,605,144 issued Feb. 25, 1997 to Simmons et al; a flexible bag containing 29-31% cupric carbonate, 26-38% sodium chloride, 24-26% citric acid, and 8-9.5% potassium chlorate that is disclosed in U.S. Pat. No. 3,980,070 issued Sep. 14, 1976 to Krupa; and an exothermic chemical system comprising of from about 30% to about 80% iron powder, from about 3% to about 25% carbonaceous material such as activated carbon, from about 0.5% to about 10% of metal salt, and from about 1% to about 40% of water, as is disclosed in U.S. Pat. No. 6,048,326 issued Apr. 11, 2000 to Davis et al. All of these patents are incorporated herein by reference.

Another aspect of this invention relates to a method to provide contrasting heat and cold applications to an injured area of the body that is fast and convenient, using a non-constrictive adhesive thermal device that can be attached to a garment, said thermal device comprising:

(a) an outer cover having one face covered at least partially with mounting adhesive as described hereinabove; and (b) one or more inner heat or cold packs containing a heating and cooling media, wherein the heat and cold packs can be easily and quickly inserted into the outer cover and interchanged from heat pack to cold pack, and vice versa, wherein the cold pack is preferably, liquid impermeable, preferably plastic inner container, preferably rectangular or square in shape, containing cooling media such as ice cubes, ice chips, crushed ice, or ice and water mixture, and wherein each said inner container is closed, e.g., sealed, on three sides and has the fourth side open, preferably having a reclosable closure, more preferably a rib and groove sealing closure (zipper closure); and wherein the optional ice-filled inner cooling pack(s) of (b) can optionally be replaced by chilled or frozen gel pack(s) and/or chemical cold pack(s), when said pack(s) are available, and wherein the heat pack is preferably a sealed fluid impermeable, preferably plastic, container containing a heating medium, such as a microwavable heating gel or water, or a container containing an exothermic chemical heating mixture.

An alternative embodiment of the present invention relates to a method to provide alternating hot and cold applications to an injured body part that is fast and convenient, using the non-constrictive thermal device hereinabove, wherein the outer cover is not self-adhesive, and the adhesive layer is provided separately as an adhesive tape, such as bandage adhesive tape or sport tape.

The present invention also relates to a method to provide alternating hot and cold applications to an injured area of the body by using adhesive to temporarily attach a thermal device of the present invention directly to the skin surface of the user, to apply said thermal device to an injured body area, said thermal device preferably comprising an outer cover having a sac structure with an open end, two or more extended peripheries with only said extended peripheries being covered with mounting adhesive, and said cover holding one or more heat packs and cold packs.

Alternatively, the present invention also relates to a method to provide alternating hot and cold applications to an injured area of the body by using preferably separate adhesive tape, preferably bandage adhesive tape, to temporarily attach a thermal device of the present invention directly to the skin surface of the user, to apply said thermal device to the injured body part, said thermal device preferably comprising an outer cover having a sac structure with an open end, said cover holding one or more heat packs and cold packs, and wherein said cover is not a self-adhering cover.

In a preferred embodiment this invention relates to a method of creating a non-constrictive alternating cooling and heating thermal device using the outer cover by filling one or more plastic zipper containers sealable by interlocking rib and groove sealing closure, with ice or an ice and water combination, to be used as cooling packs, and heating in a microwave oven one or more gel hot packs, or activating one or more exothermic chemical heating packs, to be used as heat packs, alternatively placing these thermal packs inside said outer cover, using the adhesive layer to attach the assembled alternating cold and hot thermal device to the inside or the outside of a garment, such that said alternating cold and hot thermal device is in close contact with an injured body part of the user when the garment is worn.

The present invention also relates to an article of manufacture to provide alternating hot and cold treatments comprising one or more outer covers as described hereinabove, optionally adhesive tape if the cover(s) do not have adhesive strips attached, and optionally at least one other element which is: one or more empty reclosable relatively liquid-impermeable plastic containers, or sealed, liquid impermeable plastic containers containing a cooling medium such as water, refrigeratable cooling gel, or endothermic chemical system, preferably one or more empty reclosable zipper containers, to contain a cooling medium, that can fit inside the enclosure of the outer cover; one or more hot packs, preferably a sealed fluid impermeable, preferably plastic, container containing a heating medium, such as a microwavable heating gel, or a container containing an exothermic chemical heating mixture; and/or a sealed plastic wrapper to keep the outer cover(s) and the optional inner container(s) in a hygienic, non-contaminated condition in storage and/or to prevent accidental loss of one or more of the elements, wherein the plastic wrapper can be transparent or opaque, and can be white or colored; and/or said article is optionally but preferably packaged in association with a set of instructions for use to direct the consumer to use the product properly, to ensure that the consumer knows what benefits can be achieved, and how best to obtain these benefits. The optional wrapper is preferably transparent or marked with the contents so that the article can be readily identified.

The present invention also relates to the association of instructions for use with the outer cover, the contrasting thermal device, the method, or the article of manufacture described hereinabove and hereinafter to ensure that the method to provide alternating hot and cold treatments can be practiced and the cover and/or the article be used efficiently, quickly, and effectively so as to maximize the effect of the alternating cooling and heating treatment on an injury. The set of instructions provides the information on how to use the outer cover, the inner containers, and the cooling media such as ice, as well as the cooling gel or the chemical cooling pack, and the heating medium, such as a microwavable heating gel, or a container containing an exothermic chemical heating mixture, to create a convenient non-constrictive thermal device that provides contrasting heat and cold treatments to an injury.

The set of instructions of the present invention preferably includes one or more of the following instructions: to direct the consumer to place the outer cover on a location on a garment such that the contained heating and cooling media will be in close contact with the injured area of the body when the garment is worn, with the outer cover placed either to the inside of the garment if there is room inside the garment to fit the complete thermal device and/or if the garment is composed of a thick layer, such as a jacket, or to place the outer cover on the outside of the garment if the garment is made of thin material that allows good transmission of heat to and from the injured body part, and/or if there is not enough room inside the garment, such as a pair of tight pants or a sock, then to attach the outer cover to the garment using the adhesive layer, with the open end preferably oriented on top, or optionally oriented side way, to facilitate the alternating insertion of one or more inner heating and cooling packs comprising containers containing a heating or cooling medium if the said thermal packs are not already inside the outer cover when it is attached to the garment.

The set of instructions preferably also includes instructions to direct the consumer to fill the inner container(s) with cooling media such as ice cubes, ice chips or crushed ice, then to seal the filled inner container(s), then to place the filled inner ice bag(s) in the compartment(s) of the outer cover, when the cooling packs are needed.

The set of instructions can include an instruction to direct the consumer to pre-cool one or more gel packs, or to activate one or more chemical cool packs, for use as the inner cooling packs. The set of instructions can also include an instruction to direct the consumer to pre-heat one or more gel packs using, e.g., a microwave, or to activate one or more exothermic chemical hot packs, for use as the inner heat packs.

The set of instructions can include an instruction to direct the consumer to first place a cold pack in the outer cover to apply the cold to the injured area for from about 3 minutes to about 1 hour, then replace the cold pack with a heat pack in the outer cover while the outer cover is still attached to the garment to apply the heat to the injured area for from about 3 minutes to about 1 hour, then optionally the cycle can be repeated several times with cold then hot treatments, and alternatively, the heat pack can be placed in the outer cover first to start with a hot treatment for from about 3 minutes to about 1 hour, before the cold pack for from about 3 minutes to about 1 hour, and optionally followed with several cycles of heat and cold treatments.

The set of instructions preferably includes an instruction to direct the user to wear the garment so as to apply the resulting attached thermal device over the injured body part where heating and cooling can occur.

The set of instructions can include an instruction to direct the consumer to use ice-filled inner cooling pack(s) and/or already cooled gel pack(s) or chemical cooling pack(s) as the inner cold packs, and microwaved gel packs or exothermic chemical packs as the inner heat packs. The set of instructions can include an instruction disclosing the non-constrictive nature and/or benefit of the thermal device of the present invention as compared to other thermal devices that have strapping. The instructions can also contain a suggestion to treat the injured body part by an application of the cooling medium first for a day or more, before the alternating hot and cold treatments. The set of instructions preferably comprises one or more of the hereinabove instructions.

The set of instructions for use with the outer cover, the contrasting thermal therapeutic device, the method, and/or the article of manufacture described hereinabove and hereinafter can be printed, e.g., on one or more of: the package, the wrapper, an accompanying instruction flyer or booklet, and/or communicated via print and/or electronic mass media, e.g., newspapers, magazines, radio, television, internet, circulars, etc.

The said set of instructions can be in one or more languages. The instructions can be in words, or illustrative images and/or icons preferably in combination with words. It is preferable to have the instructions contain pictorial representations of the steps in preparing and using the ice bag device to supplement, or replace the written instructions when the user is not familiar with the language(s) of the instructions.

The thermal device comprising a flexible outer cover with an adhesive attachment system that is useful in the method of the present invention is described with reference to the drawings in U.S. patent application Ser. No. 10/455,886.

II. Non-Constrictive Safety Pin Attachment System

This invention, in this aspect, relates to a method to provide alternating hot and cold applications to an injured area of the body using a flexible outer cover having a basic configuration generally similar to that described hereinbefore, with a top open end (or optionally with the open end oriented side way) to insert alternatively at least one heat pack and then, alternating, at least one cold pack, or vice versa, preferably said outer cover having an extended periphery on at least one side, preferably at two opposing sides, or at three or four sides, to permit attaching said outer cover to the inside or the outside of a garment using a plurality of safety pins, wherein "plurality" is typically from 1 to about 20 safety pins, to temporarily attach said cover, when it is alternatively filled with one or more heat and cold packs, such that said thermal packs are in close contact with an injured area of the body of a user, without the need for a strapping and/or wrapping means, when the garment is worn. Said outer cover typically comprises a piece of flexible substrate, such as a piece of fabric, more preferably said outer cover being a sac structure (or pouch structure) with one or more open ends (or sides) and optionally having two or more extended peripheries (or extended sides, or extended edges) that have a width of at least about 0.5 centimeter, preferably of at least about 1 centimeter, with the periphery extension typically has a width of from about 0.5 cm to about 10 cm, preferably from about 1 cm to about 5 cm, more preferably from about 1.5 cm to about 3 cm, and wherein said inner heat and cold packs can be interchangeably inserted quickly, easily, and conveniently through said open end(s) and/or side(s) of said outer cover. The hot and cold packs that are useful herein are described hereinbefore, and can fit inside the enclosure of the outer cover after the safety pins have been attached.

The contrasting thermal device comprising a flexible outer cover with a safety pin attachment system that is useful in the method of the present invention is described with reference to the drawings in U.S. patent application Ser. No. 10/455,885 filed Jun. 6, 2003. The outer cover can have any suitable shape such as rectangular, square, round, oval, and the like. Preferably the flexible outer cover has a generally rectangular or square configuration when flattened to facilitate storage and to more efficiently contain typical thermal packs. Typically the outer cover has two faces or sides that join together at the edges to form a sac or pouch structure having one or two open ends and three or two closed edges. The flexible outer cover is preferably a unitary structure, typically either a piece of flexible substrate, such as a piece of fabric, or said outer cover is a sac structure (or pouch structure) having one or more open sides (or ends), e.g., a sac structure (or pouch structure) with one open side or a generally tubular structure with two open sides, and optionally having two or more extended peripheries (or extended sides or extended edges) for use to attach the outer cover to the garment, using the safety pins. The inner heat and cold packs are separate structures that are not permanently attached to the outer cover. More preferably, the outer cover is either a sac structure with one open end, as depicted in FIG. 1 of U.S. patent application Ser. No. 10/455,885, or a tubular structure with two open ends, as depicted in FIG. 3 of U.S. patent application Ser. No. 10/455,885, wherein the inner thermal packs are interchangeably inserted.

The periphery of the outer cover can be extended on all four sides for use to attach said outer cover to a garment using the safety pins, or can be extended on only two or three sides, preferably two opposite sides. For a closed side, the width of its extended periphery is from the sealed line to the edge of the side, as is depicted in FIG. 3 of U.S. patent application Ser. No. 10/455,885. For an open side, the width of its extended periphery is approximately defined by the gap between the edge of the outer cover and the edge of the inner cooling pack, as is depicted in FIG. 4 of U.S. patent application Ser. No. 10/455,885. The preferred heat and cold packs are separate from the outer cover, so the direct storage of a cooling medium in the interior of the outer cover, without an inner container, as presented in FIG. 4 of U.S. patent application Ser. No. 10/455,885 is not preferred. Specific embodiments of the contrasting thermal device of the present invention which are illustrated in FIG. 1 to FIG. 3 of U.S. patent application Ser. Nos. 10/455,885, are shown with descriptions as paragraphs 100671 to 100691 on pages 7 and 8 of U.S. Pat. Appl. Pub. No. U.S. 2004/0244412 A1 Dec. 9, 2004, with the understanding that where a cold pack is shown, it can alternatively be replaced with a heat pack, and said patent application and patent application Publication are incorporated herein by reference.

In a preferred embodiment, the outer cover has two peripheries that are extended from the two opposite closed sides that are used in the attachment of the outer cover to a garment, while the open end that is preferably located on the top side remains open for an easy insertion and/or exchange of the inner heat and cold packs. Preferably the open end of the outer cover is the top open end, and that open end is preferably not closed by the safety pins so that the inner cold and heat packs can be easily and conveniently inserted and interchanged therewithin. Therefore the arrangements depicted in FIG. 7 to FIG. 9 of U.S. patent application Ser. No. 10/455, 885 are not preferred. Other preferred embodiments are described herein with reference to the drawings of this specification.

FIG. 2 of the current invention is a view of an embodiment of the contrasting thermal device of the present invention, designated as 201 comprising a flexible outer cover 211 with a tubular structure in an open configuration having one open (top) end 224, two closed sides 221 and 222, and with the bottom open side 223 closed off by a plurality of safety pins 51. The top open end 224, which can optionally be oriented side way, is used for inserting and alternatively replacing and/or alternating, (alternatingly) the thermal packs 41. A portion of cover 211 is cut away to show thermal pack 41. The outer cover 211 of the thermal device 201 is attached to garment 61 with a plurality of safety pins 51, with the pins securing the two opposing closed sides 221 and 222, and the bottom open side 223.

FIG. 3 of the current invention is a view of an alternative embodiment of the contrasting thermal device of the present invention, designated as 301 comprising a flexible outer cover 311 with a sac structure in an open configuration having one open (top) end 324, three closed sides 321, 322, and 323, and two extended peripheries 341 and 342 that are extended from the two opposing close sides 321 and 322. The top open end 324, which can optionally be oriented side way, is used for inserting and alternatingly replacing the thermal packs 41. A portion of cover 311 is cut away to show thermal pack 41. The outer cover 311 of the thermal device 301 is attached to garment 61 with a plurality of safety pins 51, with the pins securing the two extended peripheries 341 and 342.

FIG. 4 of the current invention is a plan view of an alternative embodiment of the contrasting thermal device of the present invention, designated as 401 comprising a flexible outer cover comprising a rectangular piece of flexible substrate 411 with four sides (or edges) 421, 422, 423 and 424, wherein a plurality of safety pins 51 a plurality of safety pins 51 are used to secure the three edges 421, 422, and 423 to garment 61 and form a compartment 451 to contain a thermal pack 41. A portion of cover 411 is cut away to show thermal pack 41. The top open side 424, which can optionally be oriented side way, is used for inserting and alternatingly replacing the thermal packs 41.

Any type of safety pin can be used in the ice bag device of the present invention to attach the outer cover to a garment. The most common and a preferred type of safety pin for use in the present invention are described in details in U.S. patent application Ser. No. 10/455, 885. Safety pins that are suitable for use in the present invention typically have an overall length of from about ¾ in. (about 18 mm) to about 3 in. (about 75 mm), preferably from about 1 in. (about 25 mm) to about 2½ in. (about 64 mm), more preferably from about 1¼ in. (about 32 mm) to about 2 in. (about 51 mm).

Thus the present invention also relates to a method of using safety pins to attach an alternating cold and hot thermal device to a garment such that said thermal device is in close contact with an injured body part of a user when the garment is worn, wherein said thermal device comprises a flexible outer cover having an open end that can receive one or more inner cooling packs filled with a cooling medium or one or more inner heating packs containing a heating medium, and allow the replacement by alternating thermal packs with ease and convenience, the said safety pins are used to attach the said outer cover to the said garment.

The present invention also relates to an article of manufacture to provide alternating hot and cold treatments comprising one or more outer covers as described hereinabove, optionally a plurality of safety pins, and optionally at least one other element which is: one or more empty reclosable relatively liquid-impermeable plastic containers, or sealed, liquid impermeable plastic containers containing a cooling medium such as water, refrigeratable cooling gel, or endothermic chemical system, preferably one or more empty reclosable zipper containers, to contain a cooling medium, that can fit inside the enclosure of the outer cover after the safety pins have been attached; one or more heat packs, preferably a sealed fluid impermeable, preferably plastic, container containing a heating medium, such as a microwavable heating gel, or a container containing an exothermic chemical heating mixture; and/or a sealed plastic wrapper to keep the outer cover(s) and the optional inner container(s) in a hygienic, non-contaminated condition in storage and/or to prevent accidental loss of one or more of the elements, wherein the plastic wrapper can be transparent or opaque, and can be white or colored; and/or said article is optionally but preferably packaged in association with a set of instructions for use to direct the consumer to use the product properly, to ensure that the consumer knows what benefits can be achieved, and how best to obtain these benefits. The optional wrapper is preferably transparent or marked with the contents so that the article can be readily identified.

The present invention also relates to the association of a set of instructions for use with the outer cover, the contrasting thermal device, or the article of manufacture described hereinabove for use with the alternating hot and cold treatment method to ensure that the method can be practiced and the cover and/or the article be used efficiently, quickly, and effectively so as to maximize the effect of the cooling and heating treatment on an injury. The set of instructions provides the information on how to use the outer cover, the safety pins, the inner containers, and cooling media such as ice, the cooling gel or the endothermic chemical cooling pack, for use as cold packs, as well as heating media, such as a microwavable heating gel or a container containing an exothermic chemical heating mixture, for use as hot packs, to create a convenient non-constrictive thermal device that provides contrasting cold and heat treatments to an injury.

The set of instructions can include all applicable instructions that are associated with the adhesive attachment system given herein before, such as, instructions for preparing the heat and cold packs, the order and durations for the contrasting treatments, and the like.

The set of instructions of the present invention preferably includes one or more of the following instructions: to direct the consumer to place the outer cover on a location on a garment such that the contained cold and heat packs will be in close contact with the injured area of the body when the garment is worn, with the outer cover placed either to the inside of the garment if there is room inside the garment to fit the complete thermal device and/or if the garment is composed of a thick layer, such as a jacket, or to place the outer cover to the outside of the garment if the garment is made of thin material that allows good transmission of cold to and from the injured body part, and/or if there is not enough room inside the garment, such as a pair of tight pants or a sock, then to attach the outer cover to the garment using the safety pins, leaving one or more sides of the outer cover open to insert one or more inner cold and heat packs.

Alternatively, the present invention also relates to a thermal therapeutic device comprising a flexible non-constrictive outer cover of the present invention, and a separate heat source comprising an inner container containing a heating medium to treat injuries and/or pain with heat only, without first going through a cold treatment. The present invention also relates to a heat treatment method and an article of manufacture comprising the thermal therapeutic device comprising one or more heat packs of the present invention.

The above description discloses, by way of example, some preferred embodiments of the present invention. However, persons of ordinary skill in the art are capable of creating numerous modifications within the scope of the claims. Changes in specifics of form and details can be made to the above-described embodiments. The claims and not the examples are the measure of the protected invention.

What is claimed is:

1. A therapeutic device for providing contrasting thermal treatments comprising:
   a. a flexible outer cover suitable for use at both hot and cold temperatures comprising:
      A. a sac structure with one open end, having one face covered with an adhesive layer that can be used to temporarily attach said outer cover to the inside or the outside of a garment, at a location on the garment that is in close contact with the injured area of the body, when the garment is worn, wherein said cover has dimensions to form one or more compartments suitable for containing one or more heat or cold packs, wherein said adhesive layer is suitable for use at both hot and cold temperatures, and wherein said adhesive layer is covered with a release layer or is applied immediately before use; or
      B. a piece of flexible substrate or a sac structure with one or more open sides, optionally having one or more extended peripheries, wherein said outer cover can be attached to the inside or the outside of a garment by the use of a plurality of safety pins, at a location on the garment that is in close contact with the injured area of the body, when the garment is worn, wherein each extended periphery has a width of at least about 1 centimeter, and wherein said cover has dimensions to form one or more compartments suitable for containing one or more heat or cold packs; and
   b. at least one cold pack selected from: resealable fluid impermeable plastic containers comprising an interlocking rib and groove sealing closure, optionally being a commercially available zipper bag, to contain ice or ice and water mixture; a refrigeratable cooling gel pack; or an endothermic chemical cold pack; or at least one heat pack selected from: microwavable gel bag; flexible bag containing microwave-absorbing particulate matter; water impermeable flexible bag containing chemical reactants which can be mixed to produce an exothermic heating mixture; or air permeable flexible bag containing an oxygen activated, heat generating chemical composition; and
   optionally, for B., either from about 1 to about 20 safety pins or from about 4 to about 12 safety pins; said therapeutic device optionally being for use to be attached to the inside or outside of a garment at a location on the garment that is in close contact with an injured area of the body.

2. The therapeutic device of claim 1 comprising one or more of said heat packs for providing heat treatments.

3. The therapeutic device of claim 1 wherein said adhesive layer retains acceptable adhesive properties when the temperature varies from about 0 degree centigrade to about 80 degrees centigrade.

4. An article of manufacture for use in a method treating an injured area of the body, wherein said method comprises the use of a contrasting thermal device to provide contrasting thermal treatments, wherein said device comprises a flexible outer cover suitable for use at both hot and cold temperatures comprising:
  A. a sac structure with one open end, having one face covered with an adhesive layer that can be used to temporarily attach said outer cover to the inside or the outside of a garment, at a location on the garment that is in close contact with the injured area of the body, when the garment is worn, wherein said cover has dimensions to form one or more compartments suitable for containing one or more heat or cold packs, wherein said adhesive layer is suitable for use at both hot and cold temperatures, and wherein said adhesive layer is covered with a release layer or is applied immediately before use; or
  B. a piece of flexible substrate or a sac structure with one or more open sides, optionally having one or more extended peripheries, wherein said outer cover can be attached to the inside or the outside of a garment by the use of a plurality of safety pins, at a location on the garment that is in close contact with the injured area of the body, when the garment is worn, wherein each extended periphery has a width of at least about 1 centimeter, and wherein said cover has dimensions to form one or more compartments suitable for containing one or more heat or cold packs and wherein said method involves placing first at least one cold or heat pack in the outer cover followed by removal of the pack(s) and optionally replacing by at least one heat or cold pack; wherein the article comprises either one or more outer covers A.; and/or one or more outer covers B., and optionally a plurality of safety pins; and at least one other element which is either (1) one or more cold packs, one or more heat packs, or (2) a set of instructions that tells a user how to use the cover to assemble a contrasting thermal device, and/or how to use the product properly, and/or to ensure that the user knows what benefits can be achieved, and/or how best to obtain these benefits, wherein the instructions are in one or more languages, and wherein the instructions are in words or words in combination with illustrative images and/or icons, said cover or covers, said cold packs and/or heat packs and/or said instructions are packaged together.

5. The article of claim 4 wherein said cold pack is an empty zipper bag container to be filled with ice chips or ice cubes in use; or refrigeratable cooling gel bag; or water impermeable flexible bag containing an endothermic chemical cooling system; and wherein said heat pack is microwavable gel bag; or flexible bag containing microwave-absorbing particulate matter; water impermeable flexible bag containing chemical reactants which can be mixed to produce an exothermic heating mixture; or air permeable flexible bag containing an oxygen activated, heat generating chemical composition.

6. The article of claim 4 comprising said cover A, and wherein said adhesive layer of said outer cover A, can either cover one entire face of the outer cover or cover only part of that face or comprise one or more adhesive strips; wherein said adhesive strips cover one or more edges of the outer cover; or wherein each adhesive strip has a width of at least about 1 cm; or wherein said adhesive strips cover one or more edges of the outer cover and each adhesive strip has a width of at least about 1 cm.; or wherein said outer cover optionally has a mounting adhesive layer on its face, and has from 1 to 4 extended peripheries from the edges of said outer cover, wherein each extended periphery is optionally covered with a mounting adhesive layer that can be used to temporarily attach said outer cover to a garment, in addition to or instead of the adhesive layer on the face of the outer cover, and wherein said adhesive layer is covered with a release layer; or has a periphery extended from the edge of the open end, wherein said periphery has an adhesive layer covering the reverse side of the periphery with respect to the mounting adhesive layer side, for use as a closing means to retain the hot and cold pack(s) in the outer cover; or wherein said adhesive layer is renewed after use by either using double-sided adhesive strips that are applied over the original adhesive layer or by removing the adhesive strips and replacing them with new strips; and wherein said set of instructions optionally comprises one or more of the following instructions:
  (a) place the outer cover on a location either inside or outside of a garment such that said cover is in close contact with the injured area of the body when the garment is worn; (b) attach the outer cover to the garment using the mounting adhesive layer, (c) attach the outer cover to the inside of the garment if there is room inside the garment to fit the complete alternating thermal device and/or if the garment is composed of one or more thick layers of fabrics, or attach the outer cover to the outside of the garment if the garment is made of thin material that allows good transmission of cold and heat to the injured area and/or if there is not enough room inside the garment; (d) fill one or more plastic zipper bags with ice for use as the inner cold packs; (e) pre-cool one or more gel packs for use as the inner cold packs; (f) activate one or more chemical cold pack for use as the inner cold packs; (g) place the filled inner cold pack(s) in the compartment(s) of the outer cover; (h) close the open end of the outer cover with the extended periphery covered with adhesive, when said extended periphery is available; (i) wear the garment to apply the attached alternating thermal device over the injured area; (j) apply the cold treatment to the injured area for from about 3 minutes to about 1 hour; (k) heat one or more gel bags or bags containing microwave-absorbing particulate matter in a microwave oven; (l) activate the exothermic chemical systems; (m) replace the cold packs by the heat packs; (n) apply the heat treatment to the injured area for from about 3 minutes to about 1 hour; (o) optionally the cycle can be repeated several times with cold then hot treatments; (p) alternatively, the heat pack can be placed in the outer cover first to start with a hot treatment, then said heat pack is replaced by the cold pack, and optionally followed with several cycles of heat and cold treatments; and/or (q) the instruction disclosing the non-constrictive nature and/or benefit of the contrasting thermal treatment.

7. The article of claim 4 comprising said cover B, and wherein said outer cover B, either has a generally tubular structure having two opposite open ends or a sac structure having three sealed sides and having the fourth side open, and wherein the cover optionally has one or more extended peripheries from the sealed sides; or is a piece of substrate having extended peripheries on at least three sides; and wherein said set of instructions optionally comprises one or more of the following instructions: (a) place the outer cover on a location either inside or outside of a garment such that said cover is in close contact with the injured area of the body when the garment is worn; (b) attach the outer cover to the garment using the safety pins, leaving the top side of the outer cover open to insert one or more inner cold and heat packs; (c) attach the outer cover to the inside of the garment if there is room inside the garment to fit the complete ice bag device and/or if the garment is composed of a thick layer, or attach the outer cover to the outside of the garment if the garment is made of thin material that allows good transmission of cold to the injured area and/or if there is not enough room inside the garment; (d) fill one or more plastic zipper bags with ice and seal said bags for use as the inner cooling packs; (e) pre-cool one or more gel packs for use as the inner cooling packs; (f) activate one or more chemical cool packs for use as the inner cooling pack; (g) place the filled inner cooling pack(s) in the compartment(s) of the outer cover, (h) wear the garment to apply the resulting attached alternating thermal device over the injured area, (i) apply the cold treatment to the injured area for from about 3 minutes to about 1 hour; (j) heat one or more gel bags or bags containing microwave-absorbing particulate matter in a microwave oven; (k) activate the exothermic chemical systems; (l) replace the cold packs by the heat packs; (m) apply the heat treatment to the injured area for from about 3 minutes to about 1 hour; (n) optionally the cycle can be repeated several times with cold then hot treatments; (o) alternatively, the heat pack can be placed in the outer cover first to start with a hot treatment, then said heat pack is replaced by the cold pack, and optionally followed with several cycles of heat and cold treatments; and/or (p) the instruction disclosing the non-constrictive nature and/or benefit of the contrasting thermal treatment.

8. The article of claim 4 wherein said article comprises either one or more outer covers A.; or one or more outer covers B, and optionally a plurality of safety pins; and one or more heat packs; and is packaged in association with a set of instructions that tells a user how to use the cover to assemble a heat treatment device.

9. A method for treating an injured area of the body, wherein said method comprises the use of a contrasting thermal device comprising a flexible outer cover compatible with both heat and cold and capable of holding at least one separate heat or cold pack that is either:
  A. a sac structure with one open end, having one face covered with an adhesive layer that can be used to temporarily attach said outer cover to the inside or the outside of a garment, at a location on the garment that is in close contact with the injured area of the body, when the garment is worn, wherein said cover has dimensions to form one or more compartments suitable for containing one or more heat or cold packs, wherein said adhesive layer is suitable for use at both hot and cold temperatures, and wherein said adhesive layer is covered with a release layer or is applied immediately before use; or
  B. a piece of flexible substrate or a sac structure with one or more open sides, optionally having one or more extended peripheries, wherein said outer cover can be attached to the inside or the outside of a garment by the use of a plurality of safety pins, at a location on the garment that is in close contact with the injured area of the body, when the garment is worn, wherein each extended periphery has a width of at least about 1 centimeter, and wherein said cover has dimensions to form one or more compartments suitable for containing one or more heat or cold packs, and wherein said method involves placing first at least one cold or heat pack in the outer cover followed by removal of the pack(s) and replacing by at least one heat or cold pack.

10. The method of claim 9 wherein said adhesive layer retains acceptable adhesive properties when the temperature varies from about 0 degree centigrade to about 80 degrees centigrade.

11. The method of claim 9 wherein the cold pack is optionally applied to the injured area for from about 3 minutes to about 1 hour, then replacing the cold pack with a heat pack in the outer cover to apply heat to the injured area for from about 3 minutes to about 1 hour, and optionally the cycle can be repeated several times with cold then hot treatments, and, alternatively, the heat pack can be placed in the outer cover first to start with a hot treatment for from about 3 minutes to about 1 hour, then said heat pack is replaced by the cold pack in said outer cover to treat the injured area for from about 3 minutes to about 1 hour, and optionally followed with several cycles of hot and cold treatments.

12. The method of claim 9 wherein said outer cover either has a generally rectangular or square configuration when flattened.

13. The method of claim 12 wherein said outer cover has dimensions to form one compartment for containing one heat or cold pack.

14. The method of claim 12 wherein the outer cover B, either has a generally tubular structure having two opposite open ends or a sac structure having three sealed sides and having the fourth side open; and wherein the cover optionally has one or more extended peripheries from the sealed side; or is a piece of substrate having extended peripheries on at least three sides.

15. The method of claim 9 wherein either: the outer cover A, comprising an adhesive layer is used to temporarily attach the said outer cover to a garment to alternatingly apply said cold and heat packs to an injured area of the body when the garment is worn; or the cover B, and safety pins are used to attach the outer cover to a garment to alternatingly apply said cold and heat packs to an injured area when the garment is worn without removing said cover from said garment.

16. The method of claim 15 wherein said adhesive layer of said outer cover A, can either cover one entire face of the outer cover or cover only part of that face or comprise one or more adhesive strips.

17. The method of claim 16 wherein said adhesive strips cover one or more edges of the outer cover or wherein each adhesive strip has a width of at least about 1 cm; or wherein said adhesive strips cover one or more edges of the outer cover and each adhesive strip has a width of at least about 1 cm.

18. The method of claim 17 wherein said outer cover optionally has an adhesive layer on its face, and has from 1 to 4 extended peripheries from the edges of said outer cover, wherein each extended periphery is covered with a mounting adhesive layer that can be used to temporarily attach said outer cover to a garment, in addition to or instead of the adhesive layer on the face of the outer cover, and wherein said adhesive layer is covered with a release layer; or has a periphery extended from the edge of the open end, wherein said periphery has an adhesive layer covering the reverse side of the periphery with respect to the adhesive layer side, for use as a closing means to retain the hot and cold pack(s)

in the outer cover; or wherein said adhesive layer is renewed after use by either using double-sided adhesive strips that are applied over the original adhesive layer or by removing the adhesive strips and replacing them with new strips.

19. The method of claim 9 wherein said outer cover is made of material which is either woven, knitted, crocheted, non-woven fabric of natural and/or synthetic fibers, felt, velvet, flocked material, heat-bonded plastic fiber material, solvent-laid thermally bonded plastic fiber material, open-cell plastic foam, close-cell plastic foam, porous plastic film, nonporous plastic film, rubber, paper, and/or laminated materials, and wherein said material is suitable for use at both hot and cold temperatures.

20. The method of claim 19 wherein said material retains acceptable adhesive properties when the temperature varies from about 0 degree centigrade to about 80 degrees centigrade.

21. The method of claim 9 wherein the cold pack comprises a resealable or permanently sealed flexible plastic liquid impermeable container containing a cooling medium and the heat pack comprises permanently sealed flexible plastic liquid impermeable or air permeable container containing a beating medium.

22. The method of claim 21 wherein the cooling medium is ice; ice and water combination; water refrigeratable cooling gel; or endothermic chemical cooling system; and the heating medium is water, microwavable gel material; microwave-absorbing particulate matter, chemical reactants which can be mixed to produce an exothermic beating mixture; or oxygen activated, heat generating chemical composition.

23. The method of claim 9 wherein said outer cover is suitable for containing one or more heat packs and at least one said heat pack is placed in the outer cover to provide a beat treatment.

* * * * *